(12) United States Patent
Achten

(10) Patent No.: US 8,547,541 B2
(45) Date of Patent: Oct. 1, 2013

(54) METHOD FOR THE CHARACTERIZATION OF OPTICAL PROPERTIES OF AN OPTICAL FIBER

(71) Applicant: Draka Comteq B.V., Amsterdam (NL)

(72) Inventor: Franciscus Johannes Achten, Tilburg (NL)

(73) Assignee: Draka Comteq B.V. (NL)

( * ) Notice: Subject to any disclaimer, the term of this patent is extended or adjusted under 35 U.S.C. 154(b) by 0 days.

(21) Appl. No.: 13/689,061

(22) Filed: Nov. 29, 2012

(65) Prior Publication Data

US 2013/0155391 A1 Jun. 20, 2013

(30) Foreign Application Priority Data

Dec. 15, 2011 (NL) .................................. 2007976

(51) Int. Cl.
*G01N 21/00* (2006.01)
(52) U.S. Cl.
USPC ........................................... 356/73.1
(58) Field of Classification Search
USPC ........................................... 356/73.1
See application file for complete search history.

(56) References Cited

U.S. PATENT DOCUMENTS 6,519,026 B1 * 2/2003 Holland ..................... 356/73.1
7,424,191 B2 * 9/2008 Tadakuma et al. ........... 385/122
7,869,014 B2 * 1/2011 Tadakuma et al. .......... 356/73.1

FOREIGN PATENT DOCUMENTS

JP 3-120437 A 12/1998
JP 11-287741 10/1999
JP 2008-203184 9/2008

OTHER PUBLICATIONS

Dutch Search Report dated Jul. 10, 2012 for Dutch Patent Application No. 2007976.

* cited by examiner

*Primary Examiner* — Tu Nguyen
(74) *Attorney, Agent, or Firm* — Shumaker, Loop & Kendrick, LLP

(57) ABSTRACT

A method for determining optical properties of an optical fiber including providing optical fibers having varying values of an optical property, measuring values of the optical property of the fibers, selecting one of the fibers as a reference fiber, determining the relative backscatter coefficient of the fibers compared to the reference optical fiber, correlating data obtained in step ii) with data obtained in step iv) to obtain a calibration curve showing a correlation between the Rrel and the values of the optical property of the optical fibers, measuring the Rrel of another optical fiber compared to the reference fiber, and determining a value of the optical property of the another optical fiber based on the calibration curve obtained in step v).

11 Claims, 3 Drawing Sheets

METHOD FOR THE CHARACTERIZATION OF OPTICAL PROPERTIES OF AN OPTICAL FIBER

CROSS-REFERENCE TO RELATED APPLICATION

This new U.S. utility application claims priority to Dutch Patent Application No. NL 2007976 filed Dec. 15, 2011, the entirety of which is incorporated by reference herein.

TECHNICAL FIELD AND BACKGROUND OF THE INVENTION

The present invention relates to a method for the determination of optical properties of an optical fiber, as well as the use of a method for the determination of one or more optical properties of an optical fiber. The present invention further relates to a method for selecting optical fibers for a specific configuration, particularly the selection of multimode optical fibers for use in ribbon cables, or other configurations benefitting from multimode optical fibers that are less sensitive to attenuation increase caused by bends in the fibers.

The scientific article titled "Experimental Investigation of Variation of Backscattered Power Level with Numerical Aperture in Multimode Optical Fibers", Electronics Letters, Vol. 18, pp. 130-132, 1982, discloses experiments for the determination how the backscattered power level varies with numerical aperture. This article teaches that graded-index fibers are more sensitive to such variations than step-index fibers. The experiments disclosed therein were performed by splicing together fibers of different numerical apertures (NA) and measuring the corresponding change in backscattering level and generating two curves: a loss curve and a parameter fluctuation curve. The results obtained showed that numerical apertures variations are accompanied by Rayleigh scattering variations.

JP2008203184 relates to a method, an apparatus and a program for evaluating a characteristic of an optical fiber obtained by a bidirectional OTDR measurement from both ends of the transmission path.

JP3120437 relates to a method for measuring strain from an optical waveguide in which a reference optical fiber and a test optical fiber are connected to each other and an OTDR measuring instrument is connected to the side of the fiber. The strain of the fiber can be found by specific arithmetic from the shift and the measured Brillouin frequency shift of the fiber (t).

JP11287741 relates to a method for measuring the maximum theoretical numerical aperture of an optical fiber.

Optical fibre ribbons are used for data communication applications in which a high data speed is required. The effective high data speed is obtained by parallel transmission along a plurality of glass fibres, using a correspondingly lower speed. However, in such a situation, a delay time occurs for each optical fibre that may lead to differences in the signal arrival times between respective fibre channels. Differences in arrival times can lead to a spreading between the light pulses on the various optical glass fibres, this phenomenon being referred to as "skew". Skew is the maximum difference in signal propagation time between the channels in an optical fibre ribbon, and is an important factor in determining the maximum speed of synchronous parallel data transmission.

Ribbon skew is expressed in the unit ps/m, being the maximum delay time difference per unit of length between the various fibers from the ribbon.

In most applications, a provision for compensation of ribbon skew is made in the receiver electronic circuit, referred to as "de-skewing". However, the range of de-skewing can be limited, and the circuitry leads to additional costs. For this reason, it is desirable to reduce skew in the ribbon itself. Low skew ribbons with skew performances in the range of <10 ps/m to <1 ps/m are commercially available.

Factors contributing to skew in ribbons include: (1) differences in delay time per fiber; (2) differences in delay times due to differences in wavelength of the optical systems used in the various fibers of the ribbons; and (3) differences in delay time per fiber due to the ribbon making process.

Without considering the effect of the ribbon making process, the present inventors assume that the numerical aperture value tolerance is the leading contributor of delay time differences in multimode optical fibers. The maximum value for Ge-doped multimode optical fibers is in the order of 15 ps/m. A second order impact on delay time differences is in the wavelength variation of the optical signal source, which has a maximum value on the order of 2 ps/m when the total 840 to 860 nm wavelength range is applied. Differential mode delay is a third cause of delay time differences, and can be as high as several ps/m for very low bandwidth multimode optical fibers, but can be optimized down to 0.1 or 0.3 ps/m by applying high grade bandwidth multimode optical fibers. Stated in reverse, a maximum delay time difference of 1 ps/m directly leads to a minimum requirement of the effective numerical aperture ($NA_{eff}$) change of less than 1% (i.e. $2 \times 10^{-3}$) in absolute value. Assuming a normal distribution of numerical aperture values, and choosing the "$+/-2\sigma$" value as a practical measure for the extreme values, this involves a maximum statistical variance of about $2/4 \times 10^{-3} = 0.5 \times 10^{-3}$.

A main cause for the deviation is due to measuring inaccuracy and process tolerances. The $NA_{eff}$ value is measured applying the "Far Field Scanning Method", in which a scan is made of the far field of a 2 m fiber sample illuminated by an 850 nm LED with the appropriate launching conditions. The main process influences that cause the intrinsic variation in $NA_{eff}$ are in: i) the Ge dope concentration variation at the core center line; and ii) the drawing induced variations in $NA_{eff}$ value, which are assumed to be small.

The numerical aperture values of a set of multimode optical fibers used in an optical fiber ribbon is an indicator of the skew of the ribbon. The numerical aperture values of a large batch of multimode optical fibers can be used to select multimode optical fibers for an optical fiber ribbon with low skew.

Additionally, the numerical aperture value of a multimode optical fiber is also an indicator of the macrobend sensitivity of the fiber. Macrobend sensitivity is defined as the induced attenuation, or loss in dB, when a fiber is bent to a certain bend radius over a certain number of turns. Multimode optical fibers with low macrobend sensitivity are preferred in situations where the multimode optical fiber is bent in low radii, or where the multimode optical fiber is under external stresses, such as in an optical fiber ribbon.

To determine an optical fiber delay time, also referred to as "time of flight", which can be used to determine skew for a group of fibers and macrobend induced attenuation, specific measurement equipment is required that requires extensive operator handling. In addition, the measurement of the numerical aperture or $NA_{eff}$, also requires specific measurement equipment and extensive operator handling.

BRIEF SUMMARY OF THE INVENTION

An object of the invention is to provide a reliable and reproducible method for determining one or more optical properties of an optical fiber.

Another object of the invention is to provide a method for determining one or more optical properties of an optical fiber that obviates the need for extensive manual operator handling.

A further object of the invention is to provide a method for determining one or more optical properties of an optical fiber in which the need for measurement equipment is minimized.

A still further object of the invention is to provide an accurate numerical aperture measurement for the purpose of fiber selection based on numerical aperture value.

A still further object of the present invention is to provide a method allowing for selecting multimode optical fibers from fiber stock to be applied in special ribbon cables with low skew requirements without the need for expensive, dedicated equipment.

In one embodiment, a method for the determination of one or more optical properties of an optical fiber comprises the steps of:
i) providing multiple optical fibers having expected variations in values of an optical property;
ii) measuring a value for the optical property of the optical fibers;
iii) selecting one of the optical fibers as a reference optical fiber;
iv) determining the relative backscatter coefficient (Rrel) of the optical fibers compared to the reference fiber;
v) correlating the data obtained in step ii) with the data obtained in step iv) to obtain a calibration curve showing the correlation between Rrel and the values for the optical property of the optical fibers;
vi) measuring the Rrel of another optical fiber as compared to the reference fiber; and
vii) determining a value for the optical property of the another optical fiber on the basis of the calibration curve obtained in step v).

The aforementioned method steps v) and vi) can be repeated to determine the value of the optical property for additional optical fibers.

The aforementioned method provides a method that is reproducible with low cost as compared to conventional measurement methods. In addition, the number of measurement setups is drastically reduced as compared to conventional methods for measuring optical properties.

The method can use the OTDR measurement to determine one or more of the optical properties. The method relates to the determination of Rrel from an OTDR backscatter trace, and uses the Rrel together with a calibration curve to assign fiber properties to a fiber under testing. Properties include numerical aperture (NA), delay time and macrobend induced attenuation. Prior to this method, the determination of these parameters required specific measurement setups other than OTDR, and with extensive operator handling.

In one embodiment, the optical property is chosen from the group including numerical aperture, delay time, macrobend induced attenuation and combinations thereof.

In an exemplary embodiment, determining the optical property of macrobend induced attenuation according to step ii) is performed by applying bends having a predetermined bend radius and subsequently measuring the macrobend induced attenuation of the light signal.

In another exemplary embodiment, determining the optical property of delay time according step ii) is performed using a time of flight measurement of a laser pulse travelling through a fiber having a known length. The time of light measurement can be done using a digital signal analyzer with a calibrated delay-line.

In another exemplary embodiment, determining the optical property of numerical aperture according step ii) is performed by the far field scanning method.

In a further embodiment, the optical property is numerical aperture and the delay time and/or macrobend induced attenuation are calculated using mathematical formulas based on the value determined for the numerical aperture.

The method can be used to determine fiber skew of a group of multimode optical fibers using the delay times for the group of multimode optical fibers obtained according to the present method.

The invention further relates to a method of determining the backscattering coefficient from bidirectional measurement of the splice or coupling loss between a reference MMF (REF) and the MMF under test (FUT). According to a preferred embodiment, steps iv) and vi) are carried out using an optical time domain reflectometer (OTDR) based method.

The invention further relates to the use of an OTDR based method for determining the macrobend induced attenuation and/or time delay by measuring the relative backscatter coefficient (Rrel) of the optical fiber.

The invention further relates to the use of an OTDR based method for determining the numerical aperture (NA) by measuring the relative backscatter coefficient (Rrel) of the optical fiber.

The invention further relates to a method for determining the NA by measuring the relative backscatter coefficient (Rrel) of an optical fiber by using the aforementioned OTDR based method.

The invention further relates to a method for determining the macrobend induced attenuation by measuring the relative backscatter coefficient (Rrel) of an optical fiber by using the aforementioned OTDR based method.

The invention further relates to a method for determining the time delay by measuring the relative backscatter coefficient (Rrel) of an optical fiber using the aforementioned OTDR based method.

The invention further relates to a method for determining the skew by measuring the relative backscatter coefficient (Rrel) of a group of optical fibers by using the aforementioned OTDR based method.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION OF THE INVENTION

Figure 1:
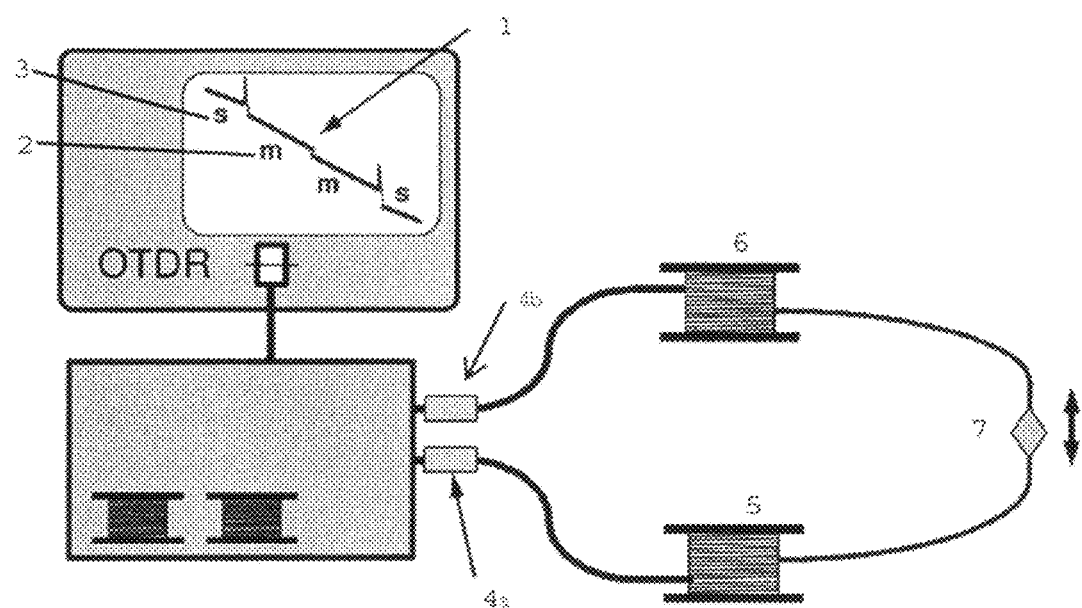
FIG. 1 shows a bi-directional OTDR test set-up for determining the relative backscatter coefficient Rrel of the multimode optical fiber (MMF) under test.

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

In one embodiment, a method for the determination of one or more optical properties of an optical fiber comprises the steps of:
  i) providing multiple optical fibers having expected variations in values of an optical property;
  ii) measuring a value for the optical property of the optical fibers;
  iii) selecting one of the optical fibers as a reference optical fiber;
  iv) determining the relative backscatter coefficient (Rrel) of the optical fibers compared to the reference fiber;
  v) correlating the data obtained in step ii) with the data obtained in step iv) to obtain a calibration curve showing the correlation between Rrel and the values for the optical property of the optical fibers;
  vi) measuring the Rrel of another optical fiber as compared to the reference fiber; and
  vii) determining a value for the optical property of the another optical fiber on the basis of the calibration curve obtained in step v).

The aforementioned method steps v) and vi) can be repeated to determine the value of the optical property for additional optical fibers.

The method can use the OTDR measurement to determine one or more of the optical properties. The method relates to the determination of Rrel from an OTDR backscatter trace, and uses the Rrel together with a calibration curve to assign fiber properties to a fiber under testing. Properties include numerical aperture (NA), delay time and macrobend induced attenuation. Prior to this method, the determination of these parameters required specific measurement setups other than OTDR, and with extensive operator handling.

The optical property is chosen from the group including numerical aperture, delay time, macrobend induced attenuation and combinations thereof.

In an exemplary embodiment, determining the optical property of macrobend induced attenuation according to step ii) is performed by applying bends having a predetermined bend radius and subsequently measuring the macrobend induced attenuation of the light signal.

In another exemplary embodiment, determining the optical property of delay time according step ii) is performed using a time of flight measurement of a laser pulse travelling through a fiber having a known length. The time of light measurement can be done using a digital signal analyzer with a calibrated delay-line.

In another exemplary embodiment, determining the optical property of numerical aperture according step ii) is performed by the far field scanning method.

In a further embodiment, the optical property is numerical aperture and the delay time and/or macrobend induced attenuation are calculated using mathematical formulas based on the value determined for the numerical aperture.

The method can be used to determine fiber skew of a group of multimode optical fibers using the delay times for the group of multimode optical fibers obtained according to the present method.

Backscattered power $P_b(z)0$) can be defined by the following equation:

$$P_b(z) = d(z)P(z)$$

Combining with (formulas from: P. Matthijsse and C. M de Blok; "Field measurement of splice loss applying the backscattering method"; Electronics Letters, Vol 15, No 24, pp 795-6; (1979))

$$d(z) \cong \frac{3}{4}\gamma_s \Delta \frac{\alpha}{\alpha+1}\langle v_g \rangle \Delta t$$

shows that the backscattered power is linearly proportional to the core contrast (Δ), which is the difference in refractive index between the center of the core and the cladding. It is also known that Δ is proportional with $NA^2$. As the influence of the core diameter is implicitly present in the other coefficients and is rather low, NA value differences between fibers dominates the absolute level of the backscattered power. The NA dominance over other parameters is enhanced further by modifying the applied OTDR method slightly in the sense that single mode fiber (SMF) launching is used. In this way, the initiating power is restricted to the lower order modes in the multimode optical fibers propagating near to the core center, i.e. in the region with the highest Ge-dope concentration which determines the theoretical NA-value ($NA_{theor}$) which can be calculated from the refractive indexes in the core center and the cladding. $NA_{theor}$ is linearly related to the measured $NA_{eff}$ value of the fiber depending on the manufacturing process of the fiber. A typical relation is $NA_{eff}=0.95 \times NA_{theor}$.

The method can be compared to measuring the splice or coupling loss between two fibers applying the bi-directional OTDR method, i.e. measuring the discontinuity at a splice or coupling point from two directions. However, whereas for splice or coupling loss measurements for the measured discontinuity values are averaged, in the present method the difference is determined as a measurement of the difference in backscattering coefficient, i.e.

$$R_{REF} - R_{FUT} = (\vec{\alpha} - \vec{\alpha})/2$$

where α is the direction dependent splice or coupling loss, and $R_{REF}$ and $R_{FUT}$ represent the backscattering coefficients of the reference multimode optical fiber MMF (REF) and the MMF under test (FUT), respectively. The backscattering coefficient is expressed in dB.

The repeatability of the test method is determined by re-measuring a fibre-to-fibre splicing or coupling 10 times. After each measurement, the full procedure of cleaving, optimization, splicing and measuring the discontinuities from two sides is repeated. To measure the discontinuity on the applied OTDR set-up, a 100 m marker distance was used and the measured loss was compensated for the fiber loss over this marker distance (fixed value of 0.051 dB). All measurements were done at 1300 nm.

A significant improvement can be achieved by applying the standard algorithm of fitting both backscatter curves with a linear curve, extrapolating these curves to the splicing or coupling position, and determining the discontinuity value from the cross-section.

In addition, further improvement on the variance can be obtained by averaging the results of multiple measurements.

Experiments carried out show a linear correlation between the actual value of the fiber $NA_{eff}$ and the measured relative backscatter coefficient (Rrel) in dB. The repeatability of the OTDR based method according to the invention is better in comparison with the standard $NA_{eff}$ test method. On the basis of the present method, it is possible to select for the purpose of low skew ribbon a group of multimode optical fiber spools with a maximum delay time difference on the order of 1 ps/m without the need to measure the absolute value of the delay time.

On basis of the present method it is also possible to select multimode optical fibers spools with a minimal macrobend induced loss without the need to measure the macrobend induced attenuation by existing methods that require specific equipment and extensive operator handlings. The existing method requires a specific launch of light into the FUT while the FUT is bent in a defined way to measure the loss of the launched light in the bent fiber.

Example 1

FIG. 1 shows a bi-directional OTDR test set-up for determining the relative backscatter coefficient Rrel of the multimode optical fiber (MMF) under test. The reference multimode fiber (REF) on a spool, indicated at reference number 6, and the various fibers-under-test (FUTs) on a spool, indicated at reference number 5, originate from a number of test fibers (750 m length). The OTDR trace 3 of the used launching single mode fiber (SMF) and the MMF under test 2 shows a high coupling loss between these fibers, i.e. in the order of 2 dB, which did not deteriorate the dynamic range of the test method. For measuring the discontinuity on the applied OTDR set-up, a 100 m marker distance was used and the measured loss was compensated for the fiber loss over this marker distance (fixed value of 0.051 dB). All measurements were done at 1310 nm. As no x-y-z micro-positioner was available with sufficient stability, the REF fiber 6 and FUTs fibers 5 were coupled by making a splice 7. The launching SMF's were coupled to the MMF's by a mechanical coupler 4a, 4b. Average splice loss 1 between the FUT and REF was 0.023 dB over more than 50 splices. The average of the difference in backscatter coefficients between the two spliced fibers was 0.016 dB for the chosen fiber samples whereas the variance was 0.009 dB.

Figure 2:
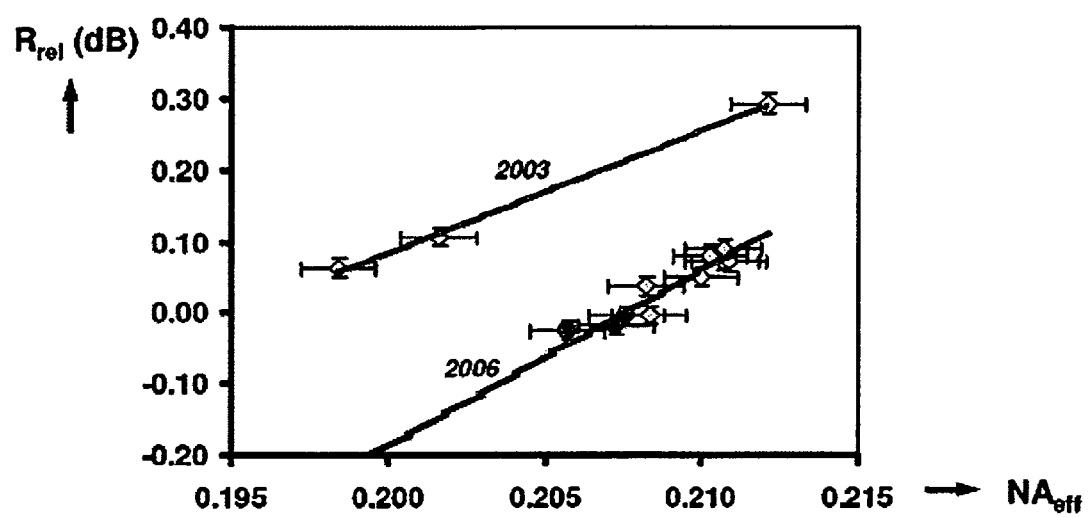
FIG. 2 shows the measured relation between NAeff (measured with existing NA measurement technique) and Rrel, the relative backscatter coefficient measured according to the method of the invention.

FIG. 2 shows the measured relation between $NA_{eff}$ (measured with existing NA measurement technique) and Rrel, the relative backscatter coefficient measured with the method according to the present invention. FIG. 2 shows two lines representing different fiber designs (2003 and 2006). The fitted line over the 2006 FUTs shows a linear relation between both parameters, i.e. the $NA_{eff}$ on the horizontal axis and the Rrel on the vertical axis. The fitted line is the calibration curve. The error bars show the wider spread over the $NA_{eff}$ values compared to the Rrel values. This justifies the use of the present method by measuring Rrel by using OTDR and subsequently computing $NA_{eff}$ from the calibration curve. The position of the fitted line depends on both the design of the reference fiber and the FUTs. This means the preference of using the same reference fiber, and, in case the design of the FUT has changed, the calibration curve must be reconstructed, i.e. the relation between Rrel, and $NA_{eff}$ must be re-measured.

The result of the present method is that once the relation between Rrel, and $NA_{eff}$ is known, it is possible to measure Rrel, and use this parameter to assign $NA_{eff}$ to the fiber under test.

Example 2

Nine multimode fibers (MMF) were bent by applying two turns over three different bend radii (5 mm, 7.5 mm and 15 mm). The macrobend induced attenuation [dB] was measured by an existing macrobend measurement technique. The standard technique involved extensive operator handling as the fibers must be carefully bent, and the launched light must fulfill precise launching conditions. In a subsequent step, these fibers were measured on Rrel according to the present method, in which the OTDR method was used, as described above. The results are shown in FIG. 3.

Figure 3:
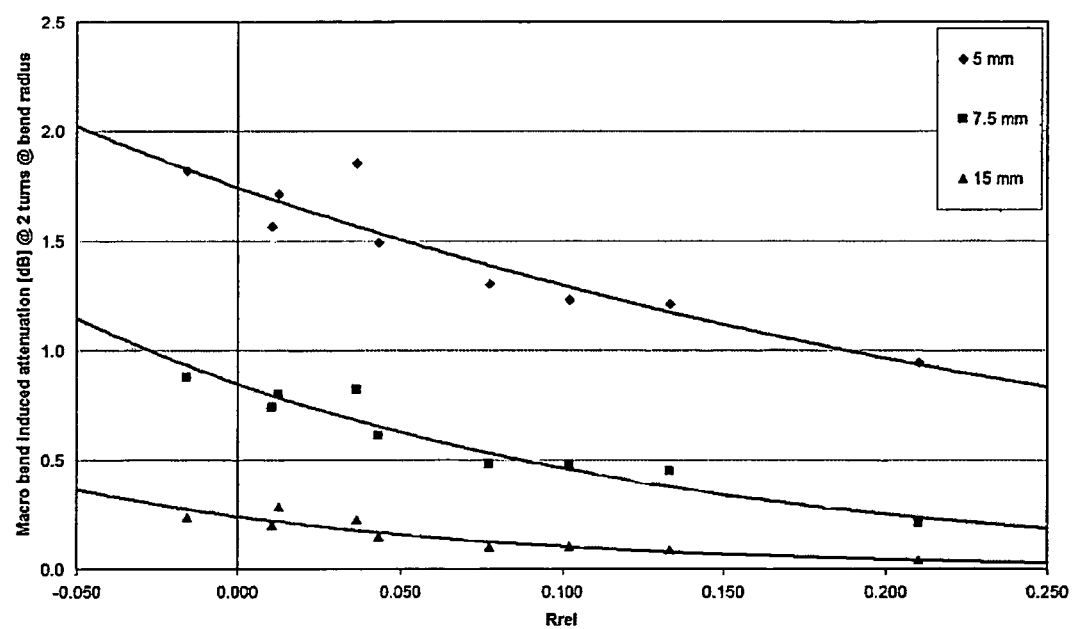
FIG. 3 shows the relation between Rrel and macrobend induced attenuation.

FIG. 3 clearly shows an increasing macrobend induced attenuation when the Rrel value decreases. On basis of this, the Rrel value serves as an indicator for determining the macrobend induced attenuation of an optical fiber.

Examples 1 and 2 clearly show that OTDR based method disclosed herein can be used for determining the $NA_{eff}$ of an optical fiber, and determining the macrobend induced attenuation, both by measuring the relative backscatter coefficient (Rrel).

The foregoing description provides embodiments of the invention by way of example only. It is envisioned that other embodiments may perform similar functions and/or achieve similar results. Any and all such equivalent embodiments and examples are within the spirit and scope of the present invention and are intended to be covered by the appended claims.

The invention claimed is:

1. A method for determining one or more optical properties of an optical fiber, comprising the steps of:
    i) providing multiple optical fibers having varying values of an optical property;
    ii) measuring values of the optical property of the optical fibers;
    iii) selecting one of the multiple optical fibers as a reference optical fiber;
    iv) determining the relative backscatter coefficient (Rrel) of the optical fibers compared to the reference optical fiber;
    v) correlating data obtained in step ii) with data obtained in step iv) to obtain a calibration curve showing a correlation between the Rrel and the values of the optical property of the optical fibers;
    vi) measuring the Rrel of another optical fiber compared to the reference fiber; and
    vii) determining a value of the optical property of the another optical fiber based on the calibration curve obtained in step v).

2. The method according claim 1, wherein steps vi) and vii) are repeated for multiple other optical fibers.

3. The method according to claim 1, wherein the optical property is selected from the group consisting of numerical aperture (NA), delay time, macrobend induced attenuation, and combinations thereof.

4. The method according to claim 3, wherein the delay time is used to calculate skew for a group of multimode optical fibers.

5. The method according to claim 1, wherein the optical property is numerical aperture and a value for the numerical aperture obtained in step vii) is used to calculate delay time and/or macrobend induced attenuation.

6. The method according to claim 1, wherein steps iv) and vi) are performed using an optical time domain reflectometer (OTDR) based method.

7. The method according to claim 6, wherein the OTDR based method comprises determining the backscattering coefficient (Rrel) from a bidirectional measurement of a splice or coupling loss between a reference multimode optical fiber and a multimode optical fiber under test.

8. The method according to claim 1, wherein the method is used to determine numerical aperture by measuring the relative backscatter coefficient (Rrel) of an optical fiber using an optical time domain reflectometer based method.

9. The method according to claim 1, wherein the method is used to determine macrobend induced attenuation by measuring the relative backscatter coefficient (Rrel) of an optical fiber using an optical time domain reflectometer based method.

10. The method according to claim 1, wherein the method is used to determine time delay by measuring the relative backscatter coefficient (Rrel) of an optical fiber using an optical time domain reflectometer based method.

11. The method according to claim 1, wherein the method is used to determine skew by measuring the relative backscatter coefficient (Rrel) of a group of optical fibers using an optical time domain reflectometer based method.

* * * * *